United States Patent [19]

vande Vis

[11] Patent Number: 5,030,001

[45] Date of Patent: Jul. 9, 1991

[54] METHOD AND APPARATUS FOR TESTING AND FURTHER PROCESSING EGGS

[75] Inventor: Johan E. vande Vis, Aalten, Netherlands

[73] Assignee: Staalkat B.V., Aalten, Netherlands

[21] Appl. No.: 524,564

[22] Filed: May 17, 1990

[30] Foreign Application Priority Data

May 17, 1989 [NL] Netherlands .................. 8901225

[51] Int. Cl.[5] .................. A01K 43/00; A01K 43/04; G01N 9/04
[52] U.S. Cl. .................. 356/53; 250/223 R; 209/510
[58] Field of Search .................. 356/52–67; 209/510–516, 656, 698; 250/223 R, 224; 382/8

[56] References Cited

U.S. PATENT DOCUMENTS 4,775,051 10/1988 van der Schoot .................. 209/510
4,805,778 2/1989 Nambu .................. 209/510

Primary Examiner—Vincent P. McGraw
Assistant Examiner—Keesee LaCharles P.
Attorney, Agent, or Firm—Griffin Branigan & Butler

[57] ABSTRACT

The invention relates to a method for testing and further processing eggs. According to the invention the eggs upon being supplied are first tested automatically for such major damage as open breaks and/or such dirt as blood stains. Further, each egg is scanned with a beam of light directed at the egg shell and the size of the aperture in the shell or any dirt is measured by a multiple transducer, viz. by counting the number of bright and dark pixels, respectively, and thus establishing the size of the damage or dirt, whereafter through comparison with set values it is automatically determined in what category of damage or contamination the egg in question is to be classified. The invention also relates to apparatus for carrying out this method.

21 Claims, 2 Drawing Sheets

METHOD AND APPARATUS FOR TESTING AND FURTHER PROCESSING EGGS

The invention relates to a method for testing and further processing eggs.

Such methods are known from various publications. Reference is made to applicant's U.S. Pat. No. 4,161,366 which discloses a method and apparatus for automatically testing eggs for defects, e.g. cracks or breaks in the shell, in which an egg is rotated and scanned by means of a plurality of beams of light. The intensity of both the light that penetrates the egg and the light that emanates from the egg is measured. In this way it is checked whether or not the egg is defective, e.g. damaged.

In practice, however, it is often important to know the size of any defect, e.g. damage or dirt, in view of the possibility of early removal of the egg from the processing system.

In view of the above, according to the invention, the method of testing and further processing eggs is first and foremost characterized in that the eggs, upon being supplied, are first tested for major defects, e.g. damage, such as open breaks, or the presence of dirt such as droppings or blood stains. The point is that in this way eggs with major defects, e.g. damage or with dirt on them are prevented from fouling the machine, thus causing a substantial accumulation of breaking eggs and making it necessary for the machine to be cleaned, which may take a great deal of time.

The eggs can be tested by using a beam of light which is directed at the egg shell of each egg and measuring the size of the aperture in the shell or the degree of contamination by counting the number of bright and dark pixels, respectively, using a multiple transducer, and thus establishing the size of the damage or the degree of contamination, whereafter through a comparison with set values it is automatically determined in what category of damage or contamination the egg in question is to be classified.

To ensure rapid measurement, in this method a beam of light may be used which moves in correspondence with the eggs supplied on rotating rollers of a roller conveyor.

Accurate measurements are obtained by using a mirror which moves at the same frequency as the passing eggs for directing the light emitted or reflected by the egg to a camera or other transducer. In this configuration both the light source and the transducer may be arranged above the moving rollers supporting the eggs. This arrangement offers a great advantage in that it does not permit dirty or leaking eggs to foul these devices.

The invention further relates to an apparatus for carrying out the method described, which apparatus comprises a supply conveyor, a portion of which can cooperate with a friction belt, at some distance above which portion a light source is arranged, whose light reflected or emitted by the egg is received by a camera (see U.S. patent application 203,102).

According to the invention this apparatus is characterized in that between the light source and the friction belt a lens is arranged which moves in correspondence with the transport rate of the eggs.

In the path of the rays reflected or emitted by the egg a mirror may be arranged which rotates at a rate which is adjusted to the transport rate of the eggs at the location of the friction belt. The movements of the lens and the mirror may be coupled by means of a linkage Easy control is obtained by driving the linkage by means of a fixedly arranged rotating cam whose circumference controls an end of a lever whose other end is rotatably connected to one member of the linkage. The aforementioned lever may be pivoted to the frame at a fixed point of rotation which is also the fulcrum of the lever moving the lens. In this way proper measurement is ensured.

When downstream of the supply track a trapdoor is arranged, the trapdoor may be indirectly controlled by a processor cooperating with the aforementioned camera. To this end the trapdoor may be part of a rotatable lever whose other end is controlled by a magnet operated by said processor.

In a further elaboration the eggs may be transported past the trapdoor by means of a closed conveyor. Such a closed conveyor is known per se from applicant's U.S. Pat. No. 4,775,051.

In a further elaboration of the invention it is observed that the apparatus for measuring the size of an aperture in the shell or the degree of contamination comprises a multiple transducer, for example a CCD camera.

Since on the rollers of a roller conveyor of an egg processing machine a plurality of eggs are positioned end to end in a closely interspaced pattern, it is impossible both for the incoming and for the outgoing light to properly reach the two ends of the egg.

To overcome this problem a further elaboration of the invention comprises means where the measuring points together with the light source and the mechanisms for moving the light beam with the transducer are provided along the roller conveyor in two positions, viz. the first for the eggs of the odd rows and the second for the eggs of the even rows. At the measuring points advancer fingers are provided which at the first measuring position push on the even eggs one roller position, so that the light beam, for instance via mirrors, can also reach the ends of the odd eggs. At the second measuring position the arrangement is for the procedure to be the other way around. It will be clear that the advancer fingers may be designed and driven in many ways.

To clarify the invention some embodiments of the apparatus for testing eggs will now be described, by way of example, with reference to the accompanying drawings, in which.

Figure 1:
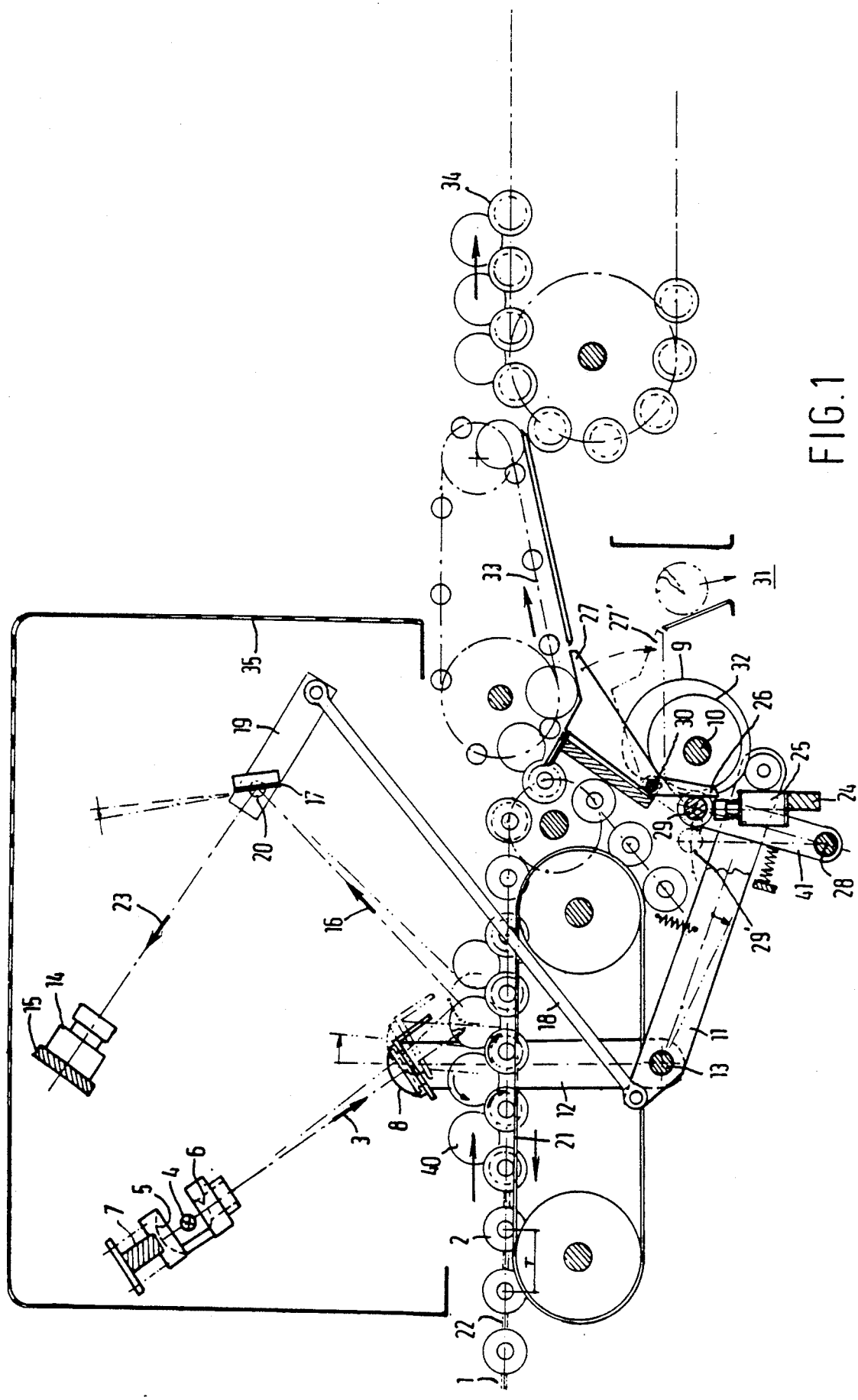
FIG. 1 is a schematic longitudinal sectional view of an apparatus for detecting open breaks in eggs or dirty eggs.

According to the drawing an "open break detector" comprises a supply conveyor 1 comprising rubber rollers 2 rotating between chains 22, for conveying eggs 40 under a beam of light 3 temporarily moving in correspondence with the eggs.

To obtain the aforementioned beam of light 3 which moves in correspondence with the eggs, a light source 4 is provided which is fixedly attached to a frame bar 7. The light source 4, by means of a concave mirror 5 and a lens 6, shines a parallel beam of light on a reciprocating lens 8, so that the light spot focussed by this lens temporarily moves in correspondence with the egg.

The movement of the lens is effected by a cam 9 on a shaft 10, the cam 9 taking care of the movement of the levers 11 and 12, which are both fixedly attached to a shaft 13 mounted for rotation in the frame.

The beam of light 3 is directed at the egg via the lens 8, and a beam of light 16 coming from the egg and also moving in correspondence with the egg is reflected by a rotating mirror 17 into a CCD camera 14 arranged on a frame bar 15. The camera 14 cooperates with a processor (not shown) which upon detecting an increase in the intensity of light, for example in the case of an open break, will produce a signal which, amplified and after a fixed time delay, operates a magnet 25 mounted on a frame bar 24, which cooperates with one end 26 of a trapdoor member 27 which in its entirety is rotatably mounted to the frame by means of a freely rotatable shaft 30. Via a link rod 18 and a link 19 rotatably connected to rod 18, the end of the lever 11 that is remote from the cam 9 is connected to a rotatable shaft 20 also mounting the mirror 17.

In this way it is ensured that simultaneously with the transport of the egg, the mirror is also moved.

Now the operation of the trapdoor 27 will be described in further detail.

The stop end 26 of the trapdoor 27 described before is controlled by a tappet 29, which is fixedly connected to a lever 41 which at a shaft 28 is rotatably mounted in a frame (not shown).

As shown further in the drawing, the tappet 29 is controlled by a cam 32 which upon each passage of an egg will force the tappet 29 shown in solid lines into the position 29' indicated by the dotted lines. When the magnet 25 is released during this movement of the tappet, the trapdoor, 27 will also be released and the eggs sitting on it will be carried off via an outlet opening 31. Otherwise, the eggs sitting on the trapdoor 27 will be conveyed over the trapdoor by conveyor 33 and to further processing stations via conveyor 34. As regards further details of the trapdoor mechanism and conveyor 33, reference may be made to U.S. Pat. No. 4,775,051, which is incorporated herein by reference.

To properly protect the light source, the optics and the camera, a protective cover 35 is arranged over them.

Since experiments have shown that the combination of light source and camera during their rotation are unable to scan the entire circumference of the egg, at the location of the "scanning path" a friction belt 21 is arranged which, during the transport of the eggs, spins the rollers 2 which are freely rotatable in the chain 22. This friction belt 21 moves in the opposite direction to that of the supply conveyor 1. This method of effecting accelerated rotation is known per se from applicant's European application 88,202,883 of Dec. 14, 1988 (corresponding to U.S. patent application 203,102).

Figure 2:
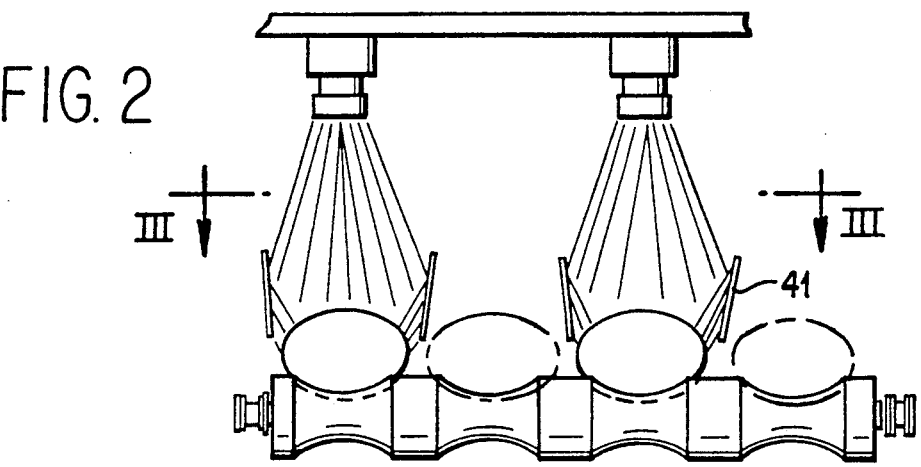
FIG. 2 shows a schematic side view of a part of another embodiment of the apparatus according to the invention.
Figure 3:
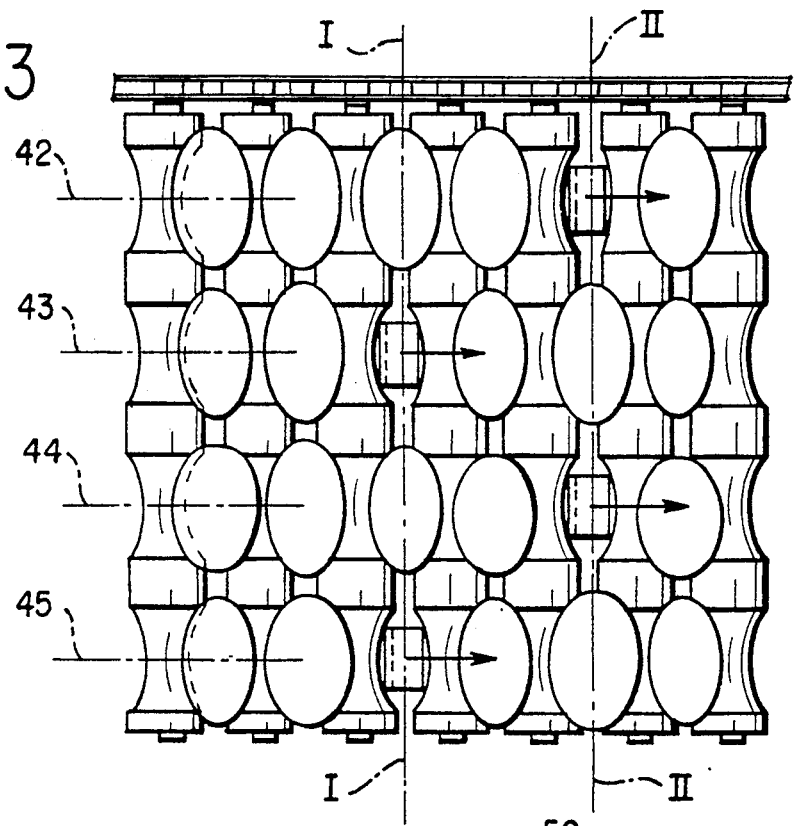
FIG. 3 shows a view taken on the line III—III of FIG. 2 with the mirrors omitted.
Figure 4:
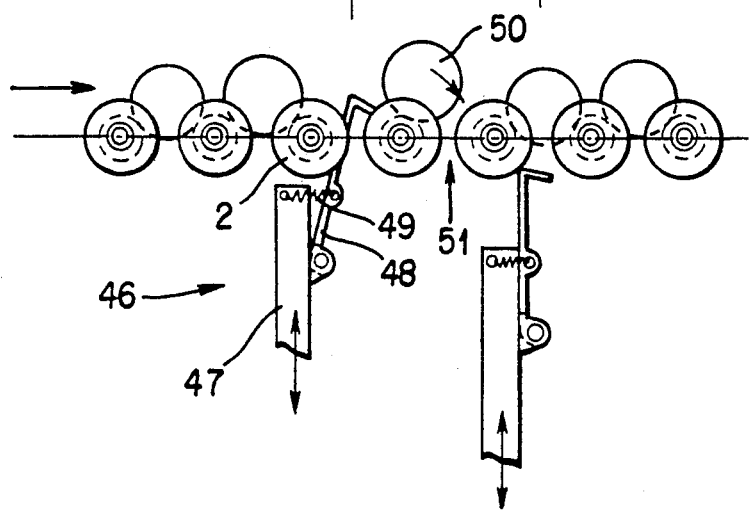
FIG. 4 is a schematic side view of the advancer fingers used in the apparatus according to FIGS. 2 and 3.

FIGS. 2, 3, and 4 show that the ends of the eggs, which are arranged closely together, are made accessible to the light by means of mirrors 41, which are arranged on the side of the rows of eggs 42–45 at an angle such that the light from the ends of the eggs is also properly received by the transducer 14.

Since there is no space for all mirrors to be arranged side by side in each row, the measuring positions I and II are arranged in staggered interrelationship, in such a way that in the even egg rows 42 and 44 the eggs are measured some rollers later than the eggs in the odd rows 43 and 45.

An advancer finger 46 comprises a holder 47 reciprocating at the frequency of the passing eggs [it is not shown how the holder 47 is driven], on which a tongue 48 is mounted for pivoting movement, retained in position by spring 49. When the advancer 46 moves up the roller 2 will move the tongue 48 forward and simultaneously move up the egg 50 until it rolls into free position 51.

I claim:

1. A method for automatically detecting and removing defective eggs, such as cracked or dirty eggs, from an array of a plurality of eggs being transported on a conveyor, comprising:
   (1) scanning each egg with a light source as each egg passes along said conveyor;
   (2) passing light emitted from or reflected from said each egg to a multiple transducer which converts the light to two or more different light levels for each pixel of the transducer;
   (3) selecting the pixels with certain light level where those pixels represent a defective portion of the egg;
   (4) determining the size of said defective portion based on the said pixels;
   (5) comparing said size with a predetermined set of values for said size and determining a classification for each defective egg; and
   (6) removing a defective egg by operating a removal means to remove a defective egg in response to the said classification of said defective egg.

2. A method according to claim 1, where the determining of the size is done by counting the numbers of said pixels.

3. A method according to claim 1, wherein the conveyor is a roller conveyor.

4. A method according to claim 3, wherein the roller conveyor has rotating rolls.

5. A method according to claim 1, characterized in that the light source and the transducer are both arranged on the same side of the conveyor.

6. A method according to claim 3, wherein said light source is a light beam and said light beam is moved in correspondence with the eggs rotating on rollers of said roller conveyor.

7. A method according to claim 1, wherein a mirror is moved at the same frequency as the eggs passing on said conveyor for deflecting the light emitted or reflected by an egg to said transducer.

8. An apparatus for automatically detecting and removing defective eggs, such as cracked or dirty eggs, from an array of a plurality of eggs being transported on a conveyor, comprising:
   (1) scanning means for scanning each egg with a light source as each egg passes along said conveyor;
   (2) multiple transducer means for converting light emitted from or reflected from each egg to two or more different light levels for each pixel of the transducer;
   (3) means for selecting the pixels with certain light level wherein those pixels represent a defective portion of the egg;
   (4) means for determining the size of said defective portion on the basis of said pixels;
   (5) means for comparing said size with a predetermined set of values for said size and determining a classification for each defective egg; and (6) removal means for removing a defective egg in response to said classification as the defective egg passes near said removal means.

9. Apparatus according to claim 8, wherein the means for determining the pixels are counting means.

10. Apparatus according to claim 8, wherein a portion of said conveyor cooperates with a friction belt for causing said eggs to rotate, and a lens is arranged between the light source and the friction belt and moves in accordance with the transport rate of the eggs.

11. Apparatus according to claim 10, wherein a mirror is arranged in a path of the reflected or emitted light and oscillates at a rate adjusted to the transport rate and the frequency of passage of the eggs at the location of the friction belt.

12. Apparatus according to claim 11, wherein the movements of the lens (17) and the mirror (17) are coupled by means of a linkage.

13. Apparatus according to claim 12, wherein the linkage is driven by means of a fixedly arranged rotating cam whose circumference controls an end of a lever whose other end is rotatably connected to a member of the linkage.

14. Apparatus according to claim 13, wherein said lever is pivoted to the frame at a fixed point of rotation which is also the fulcrum of the lever operating the lens.

15. Apparatus according to claim 8, wherein the removal means is a trapdoor and the trapdoor is controlled by a processor cooperating with the transducer.

16. Apparatus according to claim 15, wherein the trapdoor is part of a rotatable lever, an end of which is controlled by a magnet operated by said processor.

17. Apparatus according to claim 15, wherein an endless conveyor moves the eggs over the trapdoor.

18. Apparatus according to claim 8, wherein the multiple transducer means is a charged couple device camera.

19. Apparatus according to claim 8, wherein the conveyor is a roller conveyor and a plurality of eggs are arranged end to end between pairs of rollers of the roller conveyor, and advancing means are provided for advancing the eggs on even rows one roller position at a first measuring position, so that light from the light source can reach the two ends of the eggs in each odd row, and at a second measuring position the eggs of the odd rows are advanced by the advancing means one roller position so as to allow the two ends of the eggs in each even row to be measured.

20. Apparatus according to claim 19, wherein mirrors are arranged on opposite sides above the rollers of each row.

21. Apparatus according to claim 20, wherein the mirrors of the various rows are arranged in a side by side and staggered relationship, as viewed in transverse direction.

* * * * *